US011246874B1

(12) United States Patent
Brábek et al.

(10) Patent No.: US 11,246,874 B1
(45) Date of Patent: Feb. 15, 2022

(54) TREATMENT OF COVID-19

(71) Applicant: Oxygen Biotech LLC, Wilmington, DE (US)

(72) Inventors: Jan Brábek, Prague (CZ); Daniel Rösel, Prague (CZ); Karel Smetana, Prague (CZ)

(73) Assignee: Oxygen Biotech LLC, Wilmington, DE (US)

( * ) Notice: Subject to any disclaimer, the term of this patent is extended or adjusted under 35 U.S.C. 154(b) by 0 days.

(21) Appl. No.: 17/235,437

(22) Filed: Apr. 20, 2021

(51) Int. Cl.
  *A61K 31/55* (2006.01)
  *A61K 9/00* (2006.01)
  *A61P 31/14* (2006.01)

(52) U.S. Cl.
  CPC ............ *A61K 31/55* (2013.01); *A61K 9/0053* (2013.01); *A61P 31/14* (2018.01)

(58) Field of Classification Search
  CPC ..................................................... A61K 31/55
  See application file for complete search history.

(56) References Cited

U.S. PATENT DOCUMENTS

| | | |
|---|---|---|
| 5,998,402 A | 12/1999 | Miller et al. |
| 6,479,535 B1 | 11/2002 | Pickar et al. |
| 7,138,392 B2 | 11/2006 | Miller et al. |
| 7,683,051 B2 | 3/2010 | Demerson |
| 7,683,052 B2 | 3/2010 | Ali et al. |
| 8,063,041 B2 | 11/2011 | Andreella et al. |
| 8,569,483 B2 | 10/2013 | Divi et al. |
| 8,815,934 B2 | 8/2014 | Pickar et al. |
| 8,889,896 B2 | 11/2014 | Divi et al. |
| 2005/0227964 A1 | 10/2005 | Fawzi et al. |
| 2009/0137559 A1 | 5/2009 | Fawzi et al. |
| 2010/0016290 A1 | 1/2010 | Cotarca et al. |
| 2010/0310870 A1 | 12/2010 | Sanganabhatla et al. |
| 2012/0330008 A1 | 12/2012 | Divi et al. |
| 2013/0289296 A1 | 10/2013 | Divi et al. |

FOREIGN PATENT DOCUMENTS

| | | |
|---|---|---|
| CA | 2793894 A1 | 11/2013 |
| EP | 0802183 A1 | 10/1997 |
| WO | WO-2008106600 A1 | 9/2008 |
| WO | WO-2009012734 A2 | 1/2009 |
| WO | WO-2012007451 A1 | 1/2012 |
| WO | WO-2012007453 A1 | 1/2012 |

OTHER PUBLICATIONS

Smetana et al. In Vivo, 2020, 34:3027-3028.*
McGonagle et al. Autoimmunity Reviews, 2020, 19: 1-7.*
Arevalo MA, Santos-Galindo M, Lagunas N, Azcoitia I, Garcia-Segura LM. Selective estrogen receptor modulators as brain therapeutic agents. J Mol Endocrinol. Jan. 19, 2011;46(1):R1-9. doi: 10.1677/JME-10-0122. PMID: 21071476.
Brabek, et al., Interleukin-6: Molecule in the intersection of cancer, Ageing and COVID-19. International Journal of Molecular Sciences. 2020, 21, 7937. 25 Pages.
Brabek, et al., Letter to: Cytokine release syndrome in severe COVID-19, Repurposing of bazedoxifene to prevent cytokine storm in COVID-19 patients. Science E-letter; 2020: 1 Page.
Burkhardt C, Bühler L, Tihy M, Morel P, Forni M. Bazedoxifene as a novel strategy for treatment of pancreatic and gastric adenocarcinoma. Oncotarget. May 7, 2019;10(34):3198-3202. PMID: 31139333; PMCID: PMC6516716.
Castelló-Ruiz M, Torregrosa G, Burguete MC, Miranda FJ, Centeno JM, López-Morales MA, Gasull T, Alborch E. The selective estrogen receptor modulator, bazedoxifene, reduces ischemic brain damage in male rat. Neurosci Lett. Jul. 11, 2014 ;575:53-7. doi: 10.1016/j.neulet.2014.05.024. Epub May 23, 2014. PMID: 24861515.
Chen X, Tian J, Su GH, Lin J. Blocking IL-6/GP130 Signaling Inhibits Cell Viability/Proliferation, Glycolysis, and Colony Forming Activity in Human Pancreatic Cancer Cells. Curr Cancer Drug Targets. 2019;19(5):417-427. doi: 10.2174/1568009618666180430123939. PMID: 29714141; PMCID: PMC7032663.
Chen X, Wei J, Li C, Pierson CR, Finlay JL, Lin J. Blocking interleukin-6 signaling inhibits cell viability/proliferation, glycolysis, and colony forming activity of human medulloblastoma cells. Int J Oncol. Feb. 2018;52(2):571-578. doi: 10.3892/ijo.2017.4211. Epub Nov. 22, 2017. PMID: 29207075; PMCID: PMC5741369.
Flannery CA, Fleming AG, Choe GH, Naqvi H, Zhang M, Sharma A, Taylor HS. Endometrial Cancer-Associated FGF18 Expression is Reduced by Bazedoxifene in Human Endometrial Stromal Cells In Vitro and in Murine Endometrium. Endocrinology. Oct. 2016;157(10):3699-3708. doi: 10.1210/en.2016-1233. Epub Jun. 6, 2016. PMID: 27267714; PMCID: PMC5045514.
Fu W, Zhao P, Li H, Fu H, Liu X, Liu Y, Wu J, Fu W. Bazedoxifene enhances paclitaxel efficacy to suppress glioblastoma via altering Hippo/YAP pathway. J Cancer. Jan. 1, 2020 ;11(3):657-667. doi: 10.7150/jca.38350. PMID: 31942189; PMCID: PMC6959043.
Hill RA, Kouremenos K, Tull D, Maggi A, Schroeder A, Gibbons A, Kulkarni J, Sundram S, Du X. Bazedoxifene—a promising brain active SERM that crosses the blood brain barrier and enhances spatial memory. Psychoneuroendocrinology. Nov. 2020;121:104830. doi:.
Luo P, Wang Y, Zhao C, Guo J, Shi W, Ma H, Liu T, Yan D, Huo S, Wang M, Li C, Lin J, Li S, Lv J, Zhang C, Lin L. Bazedoxifene exhibits anti-inflammation and anti-atherosclerotic effects via inhibition of IL-6/IL-6R/STAT3 signaling. Eur J Pharmacol. Feb. 15, 2021;893:173822. doi: 10.1016/j.ejphar.2020.173822. Epub Dec. 23, 2020 PMID: 33347820.
Ma H, Yan D, Wang Y, Shi W, Liu T, Zhao C, Huo S, Duan J, Tao J, Zhai M, Luo P, Guo J, Tian L, Mageta L, Jou D, Zhang C, Li C, Lin J, Lv J, Li S, Lin L. Bazedoxifene exhibits growth suppressive activity by targeting interleukin-6/glycoprotein 130/signal transducer and activator of transcription 3 signaling in hepatocellular carcinoma. Cancer Sci. Mar. 2019;110(3):950-961. doi: 10.1111/cas.13940. Epub Feb. 16, 2019 Erratum in: Cancer Sci. May 2020;111(5):1862. PMID: 30648776; PMCID: PMC6398888.

(Continued)

*Primary Examiner* — Rei Tsang Shiao
(74) *Attorney, Agent, or Firm* — Wilson Sonsini Goodrich & Rosati

(57) ABSTRACT

Provided herein are methods and compositions for the treatment of COVID-19.

16 Claims, 2 Drawing Sheets

(56) References Cited

OTHER PUBLICATIONS

Naunton M, Al Hadithy AF, Brouwers JR, Archer DF. Estradiol gel: review of the pharmacology pharmacokinetics, efficacy, and safety in menopausal women. Menopause. May-Jun. 2006;13(3):517-27. doi: 10.1097/01.gme.0000191881.52175.8c. PMID: 16735950.

Ouyang Q, Zhang K, Lin D, Feng CG, Cai Y, Chen X. Bazedoxifene Suppresses Intracellular Mycobacterium tuberculosis Growth by Enhancing Autophagy. mSphere. Apr. 8, 2020;5(2):e00124-20. doi: 10.1128/mSphere.00124-20. PMID: 32269154; PMCID: PMC7142296.

Puramdas E, Singh C, Kumar V, Bhatt TD, Roy S, et al. (2016) Enhanced Solubility and Dissolution Rate of Raloxifene using Cycloencapsulation Technique. J Anal Pharm Res 2(5): 00032. DOI: 10.15406/japlr.2016.02.00032.

Sangeun Jeon, Meehyun Ko, Jihye Lee, Inhee Choi, Soo Young Byun, Soonju Park, David Shum, Seungtaek Kim. Identification of antiviral drug candidates against SARS-CoV-2 from FDA-approved drugs. bioRxiv 2020.03.20.999730;20 Pages: doi: https://doi.org/10.1101/2020.03.20.999730.

Shi W, Ma H, Liu T, Yan D, Luo P, Zhai M, Tao J, Huo S, Guo J, Li C, Lin J, Zhang C, Li S, Lv J, Lin L. Inhibition of Interleukin-6/glycoprotein 130 signalling by Bazedoxifene ameliorates cardiac remodelling in pressure overload mice. J Cell Mol Med. Apr. 2020;24(8):4748-4761. doi: 10.1111/jcmm.15147. Epub Mar. 12, 2020. PMID: 32164044; PMCID: PMC7176848.

Smetana, et al., Role of Interleukin-6 in lung complications in patients with covid-19: therapeutic implications. In Vivo 2020; 34: 1589-1592.

Wang J, Liu T, Chen X, Jin Q, Chen Y, Zhang L, Han Z, Chen D, Li Y, Lv Q, Xie M. Bazedoxifene Regulates Th17 Immune Response to Ameliorate Experimental Autoimmune myocarditis via Inhibition of STAT3 Activation. Front Pharmacol. Feb. 10, 2021; 11:613160. doi: 10.3389/fphar.2020.613160. PMID: 33643041; PMCID: PMC7903338.

Wei J, Ma L, Lai YH, Zhang R, Li H, Li C, Lin J. Bazedoxifene as a novel GP130 inhibitor for Colon Cancer therapy. J Exp Clin Cancer Res. Feb. 8, 2019;38(1):63. doi: 10.1186/s 13046-019-1072-8. Erratum in: J Exp Clin Cancer Res. Aug. 23, 2019;38(1):374. PMID: 30736824; PMCID: PMC6368818.

Xiao H, Bid HK, Chen X, Wu X, Wei J, Bian Y, Zhao C, Li H, Li C, Lin J. Repositioning Bazedoxifene as a novel IL-6/GP130 signaling antagonist for human rhabdomyosarcoma therapy. PLoS One. Jul. 3, 2017;12(7):e0180297. doi: 10.1371/journal.pone.0180297. PMID: 28672024; PMCID: PMC5495564.

Yadav A, Kumar B, Teknos TN, Kumar P. Bazedoxifene enhances the anti-tumor effects of cisplatin and radiation treatment by blocking IL-6 signaling in head and neck cancer. Oncotarget. Aug. 22, 2016;8(40):66912-66924. doi: 10.18632/oncotarget. 11464. PMID: 28978005; PMCID: PMC5620145.

Zafar E, Maqbool MF, Iqbal A, Maryam A, Shakir HA, Irfan M, Khan M, Li Y, Ma T. A comprehensive review on anticancer mechanism of bazedoxifene. Biotechnol Appl Biochem. Mar. 24, 2021. doi: 10.1002/bab.2150. Epub ahead of print. PMID: 33759222.

* cited by examiner

TREATMENT OF COVID-19

BACKGROUND

COVID-19 is an infectious disease caused by severe acute respiratory syndrome coronavirus 2 (SARS-CoV-2). Symptoms of COVID-19 include fever, cough, fatigue, breathing difficulties and loss of smell or taste. Some patients develop severe symptoms, including dyspnea, respiratory failure, shock, and multiorgan dysfunction. Patients with severe COVID-19 cases may need mechanical ventilation. Additional treatments for patients with COVID-19 are needed.

SUMMARY

In certain aspects, disclosed herein is a method of treating a subject with COVID-19, the method comprising administering bazedoxifene to the subject. In some embodiments, the subject has moderate to severe COVID-19. In some embodiments, the subject is at risk of a cytokine storm. In some embodiments, administering the bazedoxifene prevents initiation of a cytokine storm. In some embodiments, administering the bazedoxifene reduces the severity of a cytokine storm. In some embodiments, administering the bazedoxifene reduces the level of IL-6 signaling in the subject. In some embodiments, the subject is greater than 65 years of age. In some embodiments, the subject is at risk of requiring mechanical ventilation or requiring extracorporeal membrane oxygenation (ECMO). In some embodiments, administering the bazedoxifene reduces the risk of the subject requiring mechanical ventilation or ECMO.

In certain aspects, disclosed herein is a method of preventing Acute Respiratory Distress Syndrome (ARDS) in a subject, the method comprising administering bazedoxifene to the subject. In some embodiments, the subject has COVID-19. In some embodiments, the subject is at risk of a cytokine storm. In some embodiments, administering the bazedoxifene prevents initiation of a cytokine storm. In some embodiments, administering the bazedoxifene reduces the severity of a cytokine storm. In some embodiments, administering the bazedoxifene reduces the level of IL-6 signaling in the subject.

In certain aspects, disclosed herein is a method of preventing a cytokine storm in a subject, the method comprising administering bazedoxifene to the subject. In some embodiments, the subject has COVID-19. In some embodiments, administering the bazedoxifene reduces the level of IL-6 signaling in the subject.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
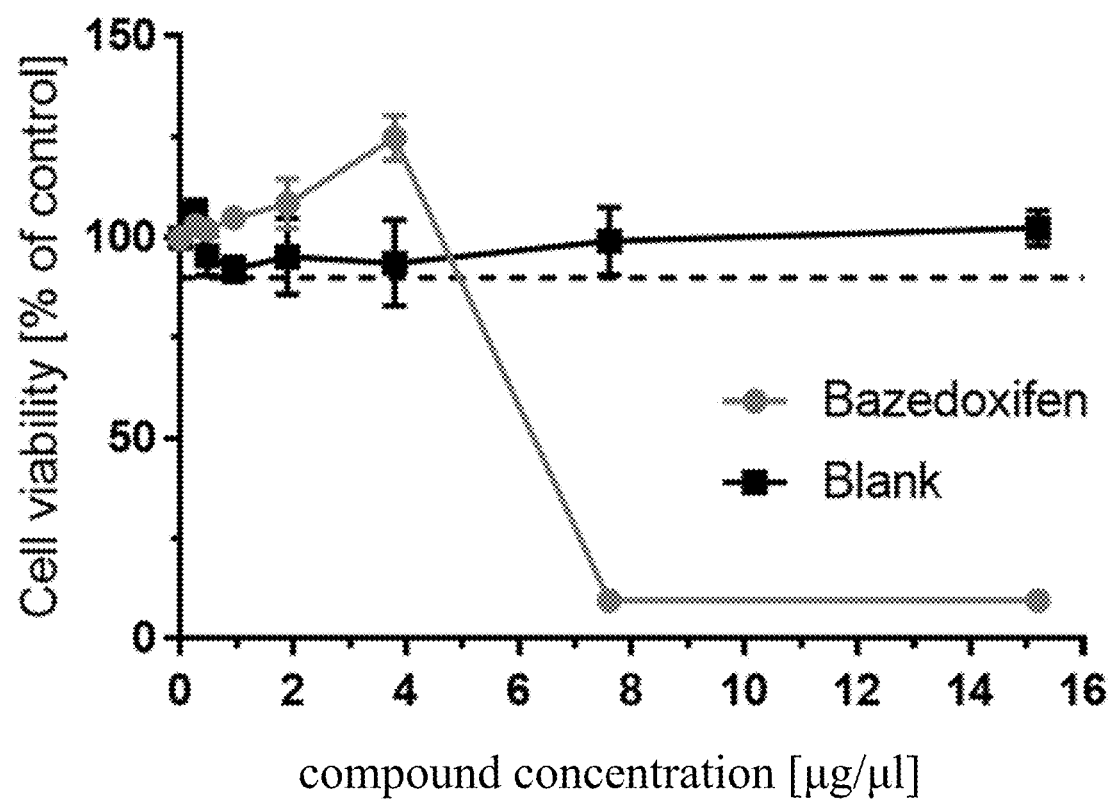
FIG. 1 depicts the viability of cultured cells treated with increasing concentrations of bazedoxifene.

COVID-19 is a transmissible respiratory disease caused by coronavirus SARS-CoV-2. The majority of infected persons are asymptomatic, or their symptoms are only mild. Some of the patients develop severe pneumonia accompanied by a risk of damage to other organs including the liver, heart, digestive system, and brain. This severe progression can lead to Acute Respiratory Distress Syndrome (ARDS), and the illness may result in the failure of respiration and the death of the patient.

COVID-19 is usually accompanied by an elevation of numerous bioactive factors such as IL-1, TNF-, IL-2, IL-7, IL-8, IL-9, IL-17 G-CSF, interferon (IFN)-, XXC-10, CCL-2 CCL-3, CCL-4, and especially IL-6, which is produced predominantly by macrophages. The severe and frequently fatal character of the disease is characterized by a high level of IL-6 and CRP in the blood or plasma of the patients. IL-6, in collaboration with other factors, influences the endothelial cells of lung capillaries, increasing their permeability for serum proteins and improving the transmigration of inflammatory cells.

Moderate to severe COVID-19 is associated with a complication referred to as cytokine storm. A cytokine storm may meet the following criteria: 1. rapid and extensive viral replication; 2. infection of airways or alveolar cells; 3. delayed IFN-response; 4. monocyte-macrophage and neutrophil accumulation. IL-6 plays a fundamental role in the advanced stage of COVID-19, where it is associated with the initiation and progression of cytokine storm, which frequently has fatal consequences for the infected person.

Blockade of the IL-6 signaling cascade can attenuate the cytokine storm in selected patients exhibiting symptoms of cytokine storm. Bazedoxifene affects the interaction of IL6 with its receptor, and the glycoprotein 130 (GP130) axis. Bazedoxifene interacts with GP130, part of the IL-6 receptor, where it prevents the binding of IL6 to the receptor.

Method of Treatment

Disclosed herein, in certain aspects, is a method of treating a subject with COVID-19, the method comprising administering bazedoxifene to the subject. Also disclosed herein is a method of preventing Acute Respiratory Distress Syndrome (ARDS) in a subject, the method comprising administering bazedoxifene to the subject. Also disclosed herein is a method of preventing a cytokine storm in a subject, the method comprising administering bazedoxifene to the subject.

Bazedoxifene

In some embodiments, administration of bazedoxifene blocks IL-6 signaling in a subject. In some embodiments, bazedoxifene interacts with GP130 and inhibits docking of IL-6 to its receptor. In some embodiments, administration of bazedoxifene reduces IL-6 signaling in a subject. In some embodiments, IL-6 signaling is reduced by at least about 1%, 5%, 10%, 20%, 30%, 40%, 50%, 60%, 70%, 80%, 90% or 100%.

In some embodiments, bazedoxifene reduces the replication of SARS-CoV-2 in susceptive cells. In some embodiments, bazedoxifene directly kills the SARS-CoV-2 virus.

In some embodiments, the subject is at risk of a cytokine storm. In some embodiments, administering the bazedoxifene reduces cytokine storm. In some embodiments, administering the bazedoxifene prevents initiation of a cytokine storm. In some embodiments, administering the bazedoxifene reduces the severity of a cytokine storm. In some embodiments, administering the bazedoxifene reduces the severity of a cytokine storm in a subject compared to a subject where bazedoxifene is not administered. In some embodiments, reducing the severity of a cytokine storm comprises reducing the severity of acute lung injury. In some embodiments, reducing the severity of a cytokine storm comprises reducing the level of inflammation. In some embodiments, the severity of a cytokine storm is reduced by at least about 1%, 5%, 10%, 20%, 30%, 40%, 50%, 60%, 70%, 80%, 90% or 100%.

In some embodiments, administering the bazedoxifene reduces the duration of a cytokine storm. In some embodiments administering the bazedoxifene reduces the duration of a cytokine storm in the subject compared to a subject where bazedoxifene is not administered.

In some embodiments, administering the bazedoxifene prevents the development of ARDS. In some embodiments, administering the bazedoxifene reduces the severity of ARDS compared to a subject where bazedoxifene was not administered. In some embodiments, administering the bazedoxifene reduces the duration of ARDS compared to a subject where bazedoxifene was not administered.

In some embodiments, the subject has moderate to severe COVID-19. In some embodiments, the subject has moderate COVID-19. In some embodiments, the subject has severe COVID-19. In some embodiments, the subject is at risk of requiring mechanical ventilation. In some embodiments, the subject is at risk of requiring extracorporeal membrane oxygenation (ECMO). In some embodiments, the subject is at risk of requiring mechanical ventilation or requiring ECMO.

In some embodiments, the subject is greater than 65 years of age. In some embodiments, the subject is at least 50 years of age, 51 years of age, 52 years of age, 53 years of age, 54 years of age, 55 years of age, 56 years of age, 57 years of age, 58 years of age, 59 years of age, 60 years of age, 61 years of age, 62 years of age, 63 years of age, 64 years of age, 65 years of age, 66 years of age, 67 years of age, 68 years of age, 69 years of age, 70 years of age, 71 years of age, 72 years of age, 73 years of age, 74 years of age, 75 years of age, 76 years of age, 77 years of age, 78 years of age, 79 years of age, 80 or more than 80 years of age.

Pharmaceutical Compositions

The compositions of the invention may be formulated into solid or liquid pharmaceutical formulations. The pharmaceutical formulations may be manufactured in any conventional manner known to a person skilled in the art. Liquid pharmaceutical formulations may include, for example, solutions, solutions for injections and solutions for infusions. The liquid pharmaceutical formulations include the pharmaceutical composition containing bazedoxifene and at least one pharmaceutically acceptable solvent, optionally also at least one pharmaceutically acceptable excipient. In some embodiments, pharmaceutically acceptable solvents include water, saline, phosphate buffered saline, and pharmaceutically acceptable buffers.

Solid pharmaceutical formulations may include, without limitations, tablets, dragees, hard capsules, soft capsules, implantable formulations, ointments, gels, suppositories and the like. The solid pharmaceutical formulations include the pharmaceutical composition containing bazedoxifene and at least one pharmaceutically acceptable excipient. In some embodiments, pharmaceutically acceptable excipients include antiadherents, binders, coatings, colorants, disintegrants, fillers, flavors, glidants, lubricants, preservatives, sorbents, sweeteners, vehicles.

Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Throughout this application, various embodiments may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used in the specification and claims, the singular forms "a", "an" and "the" include plural references unless the context clearly dictates otherwise. For example, the term "a sample" includes a plurality of samples, including mixtures thereof.

The terms "determining," "measuring," "evaluating," "assessing," "assaying," and "analyzing" are often used interchangeably herein to refer to forms of measurement. The terms include determining if an element is present or not (for example, detection). These terms can include quantitative, qualitative or quantitative and qualitative determinations. Assessing can be relative or absolute. "Detecting the presence of" can include determining the amount of something present in addition to determining whether it is present or absent depending on the context.

The terms "subject," "individual," or "patient" are often used interchangeably herein. A "subject" can be a biological entity containing expressed genetic materials. The biological entity can be a plant, animal, or microorganism, including, for example, bacteria, viruses, fungi, and protozoa. The subject can be tissues, cells and their progeny of a biological entity obtained in vivo or cultured in vitro. The subject can be a mammal. The mammal can be a human. The subject may be diagnosed or suspected of being at high risk for a disease. In some cases, the subject is not necessarily diagnosed or suspected of being at high risk for the disease.

The term "in vitro" is used to describe an event that takes places contained in a container for holding laboratory reagent such that it is separated from the biological source from which the material is obtained. In vitro assays can encompass cell-based assays in which living or dead cells are employed. In vitro assays can also encompass a cell-free assay in which no intact cells are employed.

As used herein, the term "about" a number refers to that number plus or minus 10% of that number. The term "about" a range refers to that range minus 10% of its lowest value and plus 10% of its greatest value.

As used herein, the terms "treatment" or "treating" are used in reference to a pharmaceutical or other intervention regimen for obtaining beneficial or desired results in the recipient. Beneficial or desired results include but are not limited to a therapeutic benefit and/or a prophylactic benefit. A therapeutic benefit may refer to eradication or amelioration of symptoms or of an underlying disorder being treated. Also, a therapeutic benefit can be achieved with the eradication or amelioration of one or more of the physiological symptoms associated with the underlying disorder such that an improvement is observed in the subject, notwithstanding that the subject may still be afflicted with the underlying disorder. A prophylactic effect includes delaying, preventing, or eliminating the appearance of a disease or condition, delaying or eliminating the onset of symptoms of a disease or condition, slowing, halting, or reversing the progression of a disease or condition, or any combination thereof. For prophylactic benefit, a subject at risk of developing a particular disease, or to a subject reporting one or more of the physiological symptoms of a disease may undergo treatment, even though a diagnosis of this disease may not have been made.

The section headings used herein are for organizational purposes only and are not to be construed as limiting the subject matter described.

EXAMPLES

The following examples are included for illustrative purposes only and are not intended to limit the scope of the invention.

Example 1: Antiviral Properties of Bazedoxifene

Infection of Vero Cells with SARS-CoV-2 Virus $0.15 \times 10^6$/ml Vero cells were infected with SARS-CoV-2 virus, an isolate from the environment, strain designated as S-007, provided by the Těchonin Biological Protection Department. Vero cells were then incubated in Dulbecco's Modified Eagle's Medium (DMEM) with 2% fetal bovine serum (FBS), DMSO 1 µl/ml, or in culture medium with bazedoxifene 10 µl in DMSO dosed from a starting stock solution of 10 mM bazedoxifene in DMSO, corresponding to a bazedoxifene concentration of 5.3 mg/ml. After 2 days of culture, the virus was quantified in the cell supernatant as follows.

Viral RNA was detected by 1-step RT-qPCR. Total RNA was isolated from 200 µl of supernatant of SARS-CoV-2 infected cells using magnetic beads. SARS-CoV-2 RNA was determined by amplifying the SARS-CoV-2 E-gene (Generi Biotech) using the SensiFast Probe One-Step Kit (BioLine) and Light Cycler 480 II (Roche). Viral RNA was quantified absolutely using a calibration curve.

Table 1 shows the changes in SARS-CoV-2 replication characterized by the RT-qPCR of the E-gene of SARS-CoV-2 in culture medium supplemented with DMSO, or in the presence of bazedoxifene dissolved in DMSO.

TABLE 1

Changes to SARS-CoV-2 replication

| Formulation | Concentration | E-gene No. of copies of the gene/ml | Fold decrease compared to DMSO | % of DMSO |
|---|---|---|---|---|
| DMSO | 1 µl/ml | $3.12 \times 10^{10}$ | 1.00 | 100.00 |
| bazedoxifene in DMSO | 10 µM 5.3 mg/ml | $5.39 \times 10^7$ | 578.09 | 0.17 |

Example 2 Virostatic Effect

Cytotoxicity

The toxicity of the test substance was measured in a culture of Vero-E6 cells (ATCC CRL-1586). Cells were cultured in a 96-well microtiter plate ($2 \times 10^4$ cells per well) for 24 h at 37° C. and 5% $CO_2$. Then, the test substance was added to the cells in a concentration range of 0-15.2 µg/µl, and the thus treated cells were subsequently incubated for another 48 h. The viability of the cells was then determined using the Cell Counting Kit-8 kit (Dojindo Molecular Technologies, Munich, Germany), exactly according to the manufacturer's instructions. Results are depicted in FIG. 1. The maximum non-toxic concentration of test substance in Vero-E6 cell culture was 3.8 µg/µl.

Antiviral Testing

Confluent culture of Vero-E6 cells (ATCC CRL-1586) was used to test for antiviral activity. Cells were cultured in a 96-well microtiter plate ($2 \times 104$ cells per well) for 24 h at 37° C. and 5% $CO_2$. The culture medium was then aspirated and replaced with fresh medium containing the test substance in a concentration range of 0-3.8 µg/µl. At the same time, the cells were infected with the SARS-CoV-2 virus (strain SARS-CoV-2/human/Czech Republic/951/2020) at a multiplicity of infection of 0.1. The thus treated and infected cells were incubated for 48 h at 37° C. and 5% $CO_2$. The medium was then aspirated from the culture wells and the virus titer was determined by plaque titration (Stefanik et al., Microorganisms 2021, 9 (3), 471; https://doi.org/10.3390/microorganisms9030471).

Figure 2:
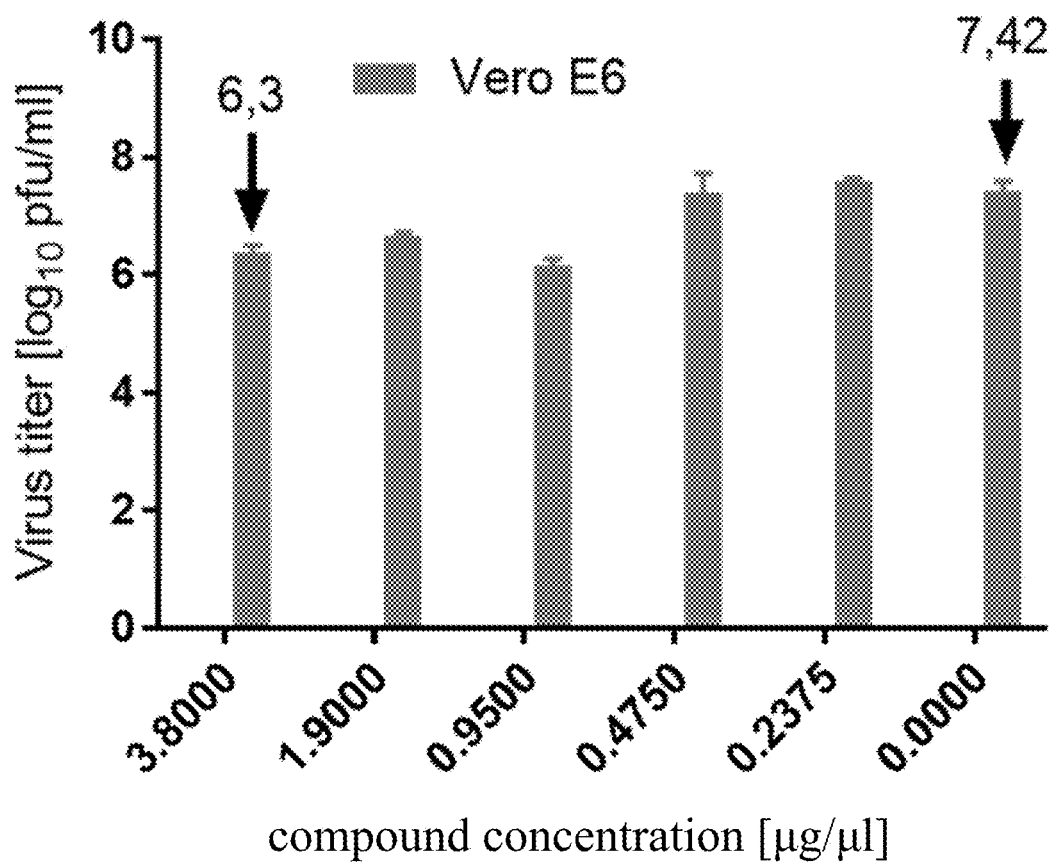
FIG. 2 depicts the effects of different concentrations of bazedoxifene on viral titer of SARS-CoV-2.

Results are depicted in FIG. 2. In Vero-E6 cell culture, an antiviral effect of the test substance was observed at the highest (non-toxic) concentrations used. While the virus titer in the control group was 7.4 $\log_{10}$ pfu/ml, the test substance-treated culture with a concentration of 3.8 µg/µl showed a mean titer of 6.3 $\log_{10}$ pfu/ml, thus decreasing the titer in the treated group by approximately 1 $\log_{10}$ pfu/ml.

Example 3: A Clinical Trial

The purpose of this study is to test the effect of bazedoxifene on the treatment of subjects with COVID-19. In addition, this study will generate data on the safety, tolerability, and pharmacokinetics of bazedoxifene on the treatment of subjects with COVID-19. Individuals will be administered placebo or bazedoxifene and monitored for 28 days of study. The following primary and secondary outcome measures will be assessed:

Primary Outcome Measures

Primary outcome measures include the safety of bazedoxifene in subjects with COVID-19.

Secondary Outcome Measures

Secondary outcome measures will include changes in clinical status of patient (using 7-point ordinal scale): on Day 0, Day 5 and 21-28 (a. Death, b. Hospitalized, on invasive mechanical ventilation or ECMO, c. Hospitalized, on non-invasive ventilation or high flow oxygen devices, d. Hospitalized, requiring supplemental oxygen, e. Hospitalized, not requiring supplemental oxygen—requiring ongoing medical, care (COVID-19 related or otherwise), f. Hospitalized, not requiring supplemental oxygen—no longer requires ongoing medical Care, g. Not hospitalized); influence of patients' clinical condition (symptom score) between baseline and day 14 (or day of discharge); frequency of patients whose condition worsens into a critical state necessitating a ventilator; time to normalization of chosen blood parameters; length of hospital stay; and rate of virus elimination from upper respiratory tract (HCD) secretions;

Inclusion Criteria

Subjects with COVID-19 will be included in this trial.

Protocol

Subjects will be administered standard of care or bazedoxifene administered daily with standard of care. Bazedoxifene will be administered orally. At the end of 28 days, subjects will be assessed by the above criteria.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

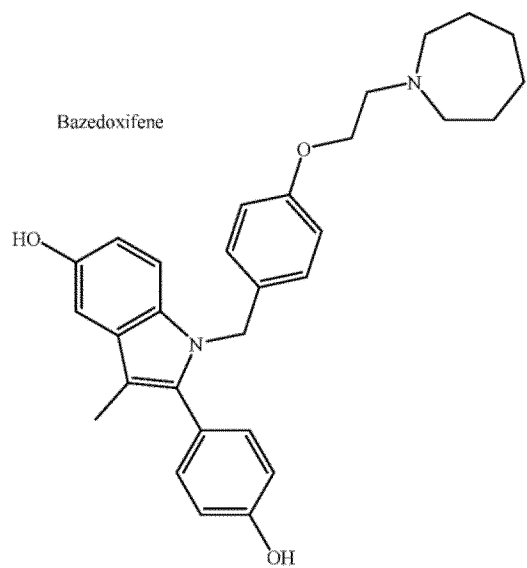

The invention claimed is:

1. A method of treating a subject with COVID-19, the method comprising administering bazedoxifene to the subject.

2. The method of claim 1, wherein the subject has moderate to severe COVID-19.

3. The method of claim 1, wherein the subject is at risk of a cytokine storm.

4. The method of claim 1, wherein administering the bazedoxifene prevents initiation of a cytokine storm.

5. The method of claim 1, wherein administering the bazedoxifene reduces the severity of a cytokine storm.

6. The method of claim 1, wherein administering the bazedoxifene reduces the level of IL-6 signaling in the subject.

7. The method of claim 1, wherein the subject is greater than 65 years of age.

8. The method of claim 1, wherein the subject is at risk of requiring mechanical ventilation or requiring extracorporeal membrane oxygenation (ECMO).

9. The method of claim 8, wherein administering the bazedoxifene reduces the risk of the subject requiring mechanical ventilation or ECMO.

10. A method of preventing Acute Respiratory Distress Syndrome (ARDS) in a subject with COVID-19, the method comprising administering bazedoxifene to the subject.

11. The method of claim 10, wherein the subject is at risk of a cytokine storm.

12. The method of claim 10, wherein administering the bazedoxifene prevents initiation of a cytokine storm.

13. The method of claim 10, wherein administering the bazedoxifene reduces the severity of a cytokine storm.

14. The method of claim 10, wherein administering the bazedoxifene reduces the level of IL-6 signaling in the subject.

15. A method of preventing a cytokine storm in a subject with COVID-19, the method comprising administering bazedoxifene to the subject.

16. The method of claim 15, wherein administering the bazedoxifene reduces the level of IL-6 signaling in the subject.

* * * * *

UNITED STATES PATENT AND TRADEMARK OFFICE
CERTIFICATE OF CORRECTION

Page 1 of 2

PATENT NO.           : 11,246,874 B1
APPLICATION NO.      : 17/235437
DATED                : February 15, 2022
INVENTOR(S)          : Brábek et al.

It is certified that error appears in the above-identified patent and that said Letters Patent is hereby corrected as shown below:

In the Specification

In the Detailed Description, Column 3 (third structure), replace:

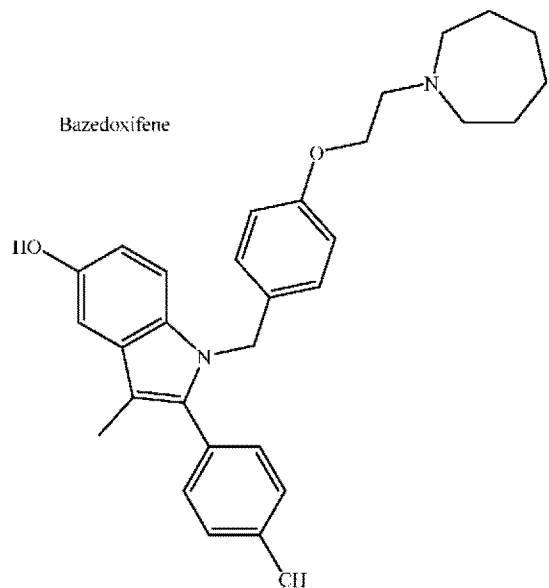

With the following structure and label:

Signed and Sealed this
Twentieth Day of September, 2022

Katherine Kelly Vidal
*Director of the United States Patent and Trademark Office*

CERTIFICATE OF CORRECTION (continued)
U.S. Pat. No. 11,246,874 B1